US009005994B2

(12) United States Patent
Huo

(10) Patent No.: US 9,005,994 B2
(45) Date of Patent: Apr. 14, 2015

(54) METHODS FOR BIOMOLECULE AND BIOMOLECULE COMPLEX (BMC) DETECTION AND ANALYSIS AND THE USE OF SUCH FOR RESEARCH AND MEDICAL DIAGNOSIS

(75) Inventor: Qun Huo, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 21 days.

(21) Appl. No.: 13/522,391

(22) PCT Filed: Jan. 12, 2011

(86) PCT No.: PCT/US2011/021002
§ 371 (c)(1),
(2), (4) Date: Oct. 10, 2012

(87) PCT Pub. No.: WO2011/088128
PCT Pub. Date: Jul. 21, 2011

(65) Prior Publication Data
US 2013/0052661 A1    Feb. 28, 2013

Related U.S. Application Data

(60) Provisional application No. 61/294,877, filed on Jan. 14, 2010, provisional application No. 61/407,038, filed on Oct. 27, 2010.

(51) Int. Cl.
*G01N 33/543*    (2006.01)
(52) U.S. Cl.
CPC ............................... *G01N 33/54346* (2013.01)
(58) Field of Classification Search
None
See application file for complete search history.

(56) References Cited

U.S. PATENT DOCUMENTS 4,490,473 A * 12/1984 Brunhouse .................... 436/518
4,762,413 A    8/1988 Namba et al.
5,922,537 A *  7/1999 Ewart et al. .................. 435/6.11

(Continued)

FOREIGN PATENT DOCUMENTS

WO    WO 94/13835       6/1994
WO    WO/2008/008785 A2  1/2008

(Continued)

OTHER PUBLICATIONS

A One-Step Homogeneous Immunoassay for Cancer Biomarker Detection Using Gold Nanoparticle Probes Coupled with Dynamic Light Scattering Xiong Liu,Qiu Dai,Lauren Austin,Janelle Coutts,Genevieve Knowles,Jianhua Zou,Hui Chen, and, and Qun Huo Journal of the American Chemical Society 2008 130 (9), 2780-2782.*

(Continued)

*Primary Examiner* — Chris L Chin
(74) *Attorney, Agent, or Firm* — Timothy H. Van Dyke; Beusse, Wolter, Sanks & Maire, P.A.

(57) ABSTRACT

The present application pertains to improved methods of detecting biomolecules in a biological sample (or system), In particular, embodiments discussed herein allow for the detection of biomolecule complexes. The embodiments enable for the first time the elucidation of the significance of biomolecule complexes for certain disease states, which in turn enables the diagnosis of disease states based on the identity and complexing level of a biomolecule complex in a particular biological sample.

16 Claims, 7 Drawing Sheets

(56) References Cited

U.S. PATENT DOCUMENTS

| | | | |
|---|---|---|---|
| 6,423,551 B1 * | 7/2002 | Weiss et al. | 436/518 |
| 6,548,264 B1 * | 4/2003 | Tan et al. | 435/7.21 |
| 6,699,723 B1 * | 3/2004 | Weiss et al. | 436/518 |
| 2006/0014172 A1 | 1/2006 | Muller et al. | |
| 2008/0085508 A1 | 4/2008 | Wei et al. | |

FOREIGN PATENT DOCUMENTS

| | | |
|---|---|---|
| WO | WO/2009/040652 A2 | 4/2009 |
| WO | WO/2009/117168 A2 | 9/2009 |

OTHER PUBLICATIONS

Probing BSA Binding to Citrate-Coated Gold Nanoparticles and Surfaces Scott H. Brewer, Wilhelm R. Glomm, Marcus C. Johnson, Magne K. Knag, and, and Stefan Franzen Langmuir 2005 21 (20), 9303-9307.*

Ferro et al., Tumour Markers in Prostatic Carcinoma. A Comparison of Prostate-specific Antigen with Acid Phosphatase, British Journal of Urology, 60, 69-73, 1987, and in further view of US 4490473, Dec. 25, 1984.*

Liu, X. et al. "A One-step homogeneous immunoassay for cancer biomarker detection using gold nanoparticle probes coupled with dynamic light scattering." J. Am. Chem. Soc. 2008, vol. 130, pp. 2780-2782.

Dai, Q. et al, "A one-step highly sensitive method for DNA detection using dynamic light scattering." J. Am. Chem. Soc. 2008, vol. 130, pp. 8138-8139.

Liu, et al. "A washing-free and amplification-free one-step homogeneous assay for protein detection using gold nanoparticle probes and dynamic light scattering." J. Immunol. Method 2009, vol. 349, pp. 38-44.

Jans, H., et al. "Dynamic light scattering as a powerful tool for gold nanoparticle bioconjugation and biomolecular binding study." Anal. Chem. 2009, vol. 81, pp. 9425-9432.

Austin, L., et al. "An immunoassay for monoclonal antibody isotyping and quality analysis using gold nanoparticles and dynamic light scattering." 2010, American Biotechnology Laboratory, 2010, 22, No. vol. 3, pp. 8-12.

Bogdanovic, et al. "a new platform technology for biomolecular detection and analysis using gold nanoparticle probes coupled with dynamic light scattering." SPIE Proceedings, (2010), 7674 (Smart Biomedical and Physiological Sensor Technology), 767408/1-767408/9.

Bogdanovic, J. et al, "A label-free nanoparticle aggregation assay for protein complex/aggregate detection and analysis." Anal. Biochem. 2010, vol. 405, pp. 96-102.

Huo, Q "Protein complexes/aggregates as potential cancer biomarker revealed by a nanoparticle aggregation immunoassay." Colloids Surf. B. 2010, vol. 78, pp. 259-265.

Jaganathan, S et al. "A functional nuclear epidermal growth factor receptor, Src and Stat3 heteromeric complex in pancreatic cancer cells." Plos One, 2010, submitted.

Huo, Q.; et al. "A facile nanoparticle immunoassay to detect multiple biomarkers in serum samples." Nanomedicine: Nanotechnology, Biology and Medicine, 2010, submitted.

* cited by examiner

5 A

5 B

US 9,005,994 B2

METHODS FOR BIOMOLECULE AND BIOMOLECULE COMPLEX (BMC) DETECTION AND ANALYSIS AND THE USE OF SUCH FOR RESEARCH AND MEDICAL DIAGNOSIS

CROSS-REFERENCE TO RELATED APPLICATIONS

This application is related to U.S. Provisional Application No. 61/294,877; filed Jan. 14, 2010 and U.S. Provisional Application 61/407,038 filed Oct. 27, 2010, and to which priority is claimed under 35 USC §119.

INTRODUCTION

Biomolecular interactions such as protein-protein and protein-DNA interactions play an essential role in almost all cellular functions. Many intracellular biochemical processes are triggered by the assembly of biomolecules including proteins, DNAs and RNAs into biomolecule complexes (BMC), providing a means to control the myriad of biochemical processes for the efficient management of vital biological responses. The detection and analysis of these biomolecule complexes is not only critical for understanding the mechanisms of diseases, but also provide new methods and approaches for diagnosis and treatment of the diseases.

While a large number of bioanalytical techniques exist for detecting and analyzing the concentrations of individual biomolecules, techniques available for studying biomolecular interactions and for biomolecule complex detection and analysis are rather limited and inadequate to meet the demands and challenges of biomolecular research and medical diagnosis. Many traditional techniques such as co-immunoprecipitation, immunoaffinity chromatography, and yeast two-hybrid assays involve complicated assay procedures, require a large volume of samples (100s μL), and take hours to days to obtain the results. Furthermore, these traditional techniques can only reveal the identities of the binding partners, and are not capable of providing the kinetic binding information. More recent techniques, such as fluorescence-based techniques and surface plasmon resonance (SPR) enable both detection and kinetic binding study of biomolecular interactions and complex formation, but have limitations, such as labeling, that may affect or destroy the structure and binding activity of the biomolecules, or in the case of SPR, the need for a solid-phase based technique (not solution-based assay) and the high cost.

DETAILED DESCRIPTION

The present patent application discloses several new methods to detect and analyze biomolecule complexes (BMC) and use of such for medical diagnosis. For the purpose of this application, biomolecule complex is defined as one biomolecule subunit such as proteins, DNAs, RNAs, carbohydrates bound with at least another biomolecule through covalent or non-covalent chemical bonding. An individual biomolecule or biomolecule subunit is defined as a monomer. Furthermore, two types of biomolecule complexes are specifically exemplified here: one is heterogeneous complex made from one biomolecule and at least another different biomolecule, and a second one is a homogenous complex made from at least two same biomolecules or biomolecule subunits. Also for the purpose of this application, each molecule component in the complex is defined as "binding partner". This application mainly uses proteins as an example of biomolecules, however, the methods disclosed here can be applied for any other types of biomolecule complexes such as protein-DNA, protein-RNA, DNA-DNA, DNA-RNA complexes. Naturally, the embodiments disclosed herein may be used to detect biomolecules that are not complexed or aggregated.

For the purpose of this application, nanoparticles in this application refer to particles with a diameter ranging from 1 nm to 10,000 nm, preferably 1-1000 nm. The new methods and system embodiments disclosed herein are an extension of the ground breaking work disclosed in PCT/US09/30087; filed Jan. 5, 2009.

It should be borne in mind that the type of nanoparticle referred in the present patent application is not limited to metal nanoparticles. The particle size measurement technique in this application is not limited to dynamic light scattering. Furthermore in some embodiments as described below, other detection techniques may be used to detect the nanoparticle clustering caused by biomolecular complex interactions.

Biological samples that can be tested using the method embodiments taught herein include, but are not limited to, are tissue, tissue lysates, tissue fluids, cells, cell lystates, cell culture media, blood, urine, stool, semen, fluid secreted from breast, saliva, sputum, or circulating tumor cells; and/or products derived from the above biological samples after chemical, physical, or biological treatments. Reference to diseased or non-diseased samples herein refers to biological samples in or derived from a subject having a disease state or a non-diseased state, respectively.

Figure 1:
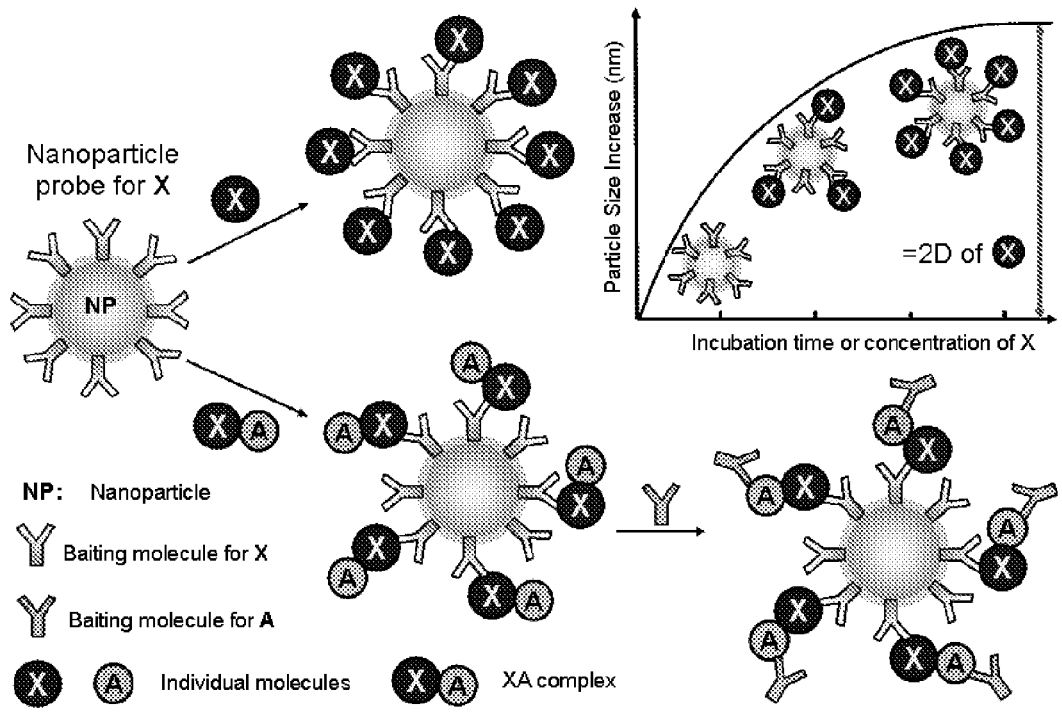
FIG. 1 shows a schematic of a first embodiment of a target molecule detection system.
Figure 2:
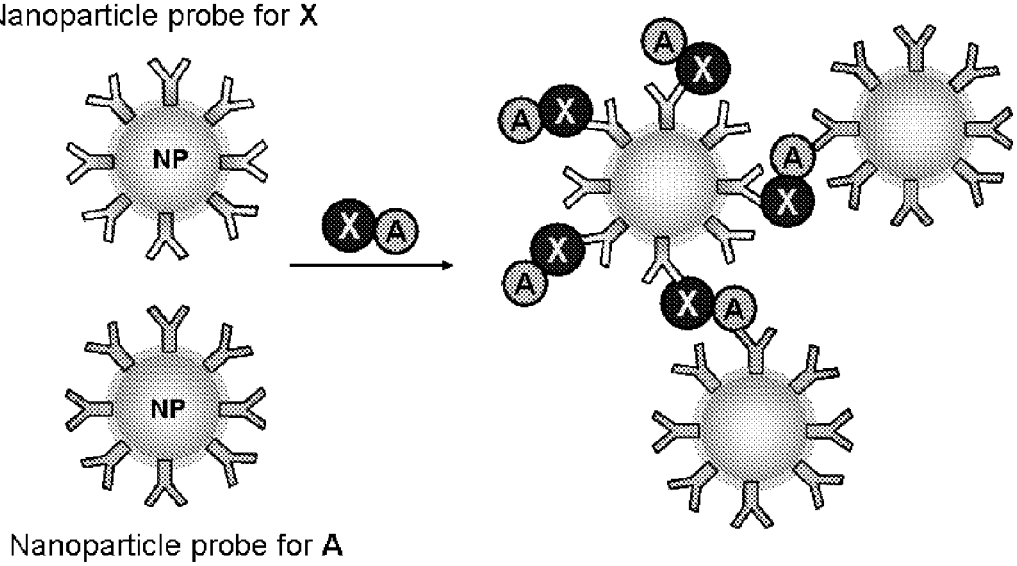
FIG. 2 shows a schematic of a second embodiment of a target molecule detection system.
Figure 3:
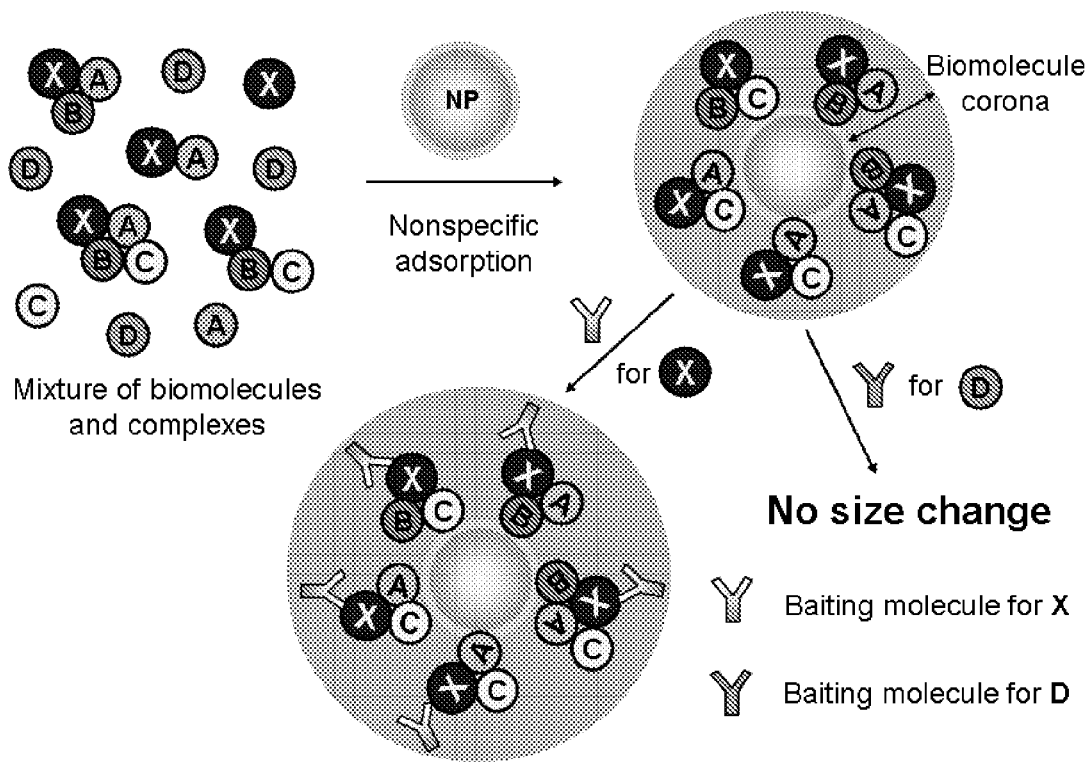
FIG. 3 shows a schematic of a third embodiment of a target molecule detection system.

FIGS. 1-3 provide schematics of three embodiments for detecting biomolecules. In one embodiment (FIG. 1), the invention involves a nanoparticle (preferably gold or silver nanoparticle) that is coated with a layer of "baiting" biomolecule. A "baiting molecule" as used herein means a molecule that can specifically bind with another biomolecule through non-covalent chemical interactions. Antibody is an example of "baiting molecule". Single strand DNA is another example of a "baiting molecule". The baiting molecule will bind with a specific target molecule X in the sample. This baiting molecule-coated nanoparticle is referred to herein as "nanoparticle probe". By contacting the nanoparticle probe solution with a sample solution, a target molecule X and/or its complexes will bind with the nanoparticle probe, causing nanoparticle probe size increase or nanoparticle clustering. Such nanoparticle size change in the assay solution can be measured by dynamic light scattering or other particle size analysis techniques to reveal the presence of target protein or protein complexes in the sample solution. The size measurement can be done continuously to reveal the binding kinetics as illustrated in the graph in FIG. 1. The binding constant or binding energy between the baiting molecule and the target molecule or complex can be obtained by fitting the binding curve into a Langmuir adsorption model using Langmuir equation. When the binding reaches a saturated level, the size of the target molecule X and/or its complex may be revealed from the average particle size change or particle size distribution change. The particle size change can be used to obtain the concentration of molecule X in the sample solution. Furthermore, by designing the assay so that a saturated binding between molecule X and the nanoparticle probe is achieved, the net increase of the particle size at saturated binding should be equal to twice of the diameter (2D) of the target molecule X. From this analysis, the size of molecule X can be obtained. If target molecule X formed complexes with other biomolecules, then the nanoparticle size increase will exceed the 2D value of X. In this case, the obtained size information of molecule X can be used to deduce the complex status and level of molecule X.

As a variation to this embodiment, the same nanoparticle could contain more than one type of baiting molecules for different target molecules. For example, baiting molecule for X and A can be both immobilized on the nanoparticle and such nanoparticle can bind with more than one type of target molecule from sample solution.

Furthermore, by adding a second step to the assay, the binding partner of the biomolecular complex can be further revealed through a screening analysis. After the first step of the assay, a solution of baiting molecule that can specifically bind with an interested binding partner molecule A will be added to the assay solution. The nanoparticles may or may not need to be isolated from the rest of the assay solution before conducting the second step of the assay. If the interested potential binding partner A is present on the nanoparticles, the binding of the baiting molecule for target molecule A to the nanoparticle will cause a further increase of the nanoparticle size or nanoparticle cluster formation, therefore, confirming that molecule A and molecule X formed a biomolecular complex.

Alternatively, the method can include the successive exposure of the assay solution to baiting molecule for target molecule A without conducting particle analysis after exposure to the nanoparticle probe with the biological sample. Based on the particle characteristics, one can determine whether baiting molecule for target molecule A binds to the nanoparticle probe presumably already having target molecule X bound thereto. From this, it can be deduced that the biomolecule complex includes target molecule X complexed to target molecule A.

In a second embodiment (FIG. 2), the assay is designed so that same or different nanoparticle probes will bind with a biomolecule complex from different sites of the complex to form nanoparticle clusters. In the illustration, two nanoparticle probes for two biomolecules X and A are shown. For illustration purpose, the complex shown here is a two-molecule complex, but the complex can include as many molecules as possible. The two nanoparticle probes may be mixed simultaneously or sequentially with the sample solution. When used simultaneously, the assay will lead to nanoparticle dimer or cluster formation if a biomolecule complex XA is present in the sample solution. The average particle size and/or particle size distribution will provide quantitative information on the complexing level of XA. Complexing level can mean both concentration of the complex XA and the size of the complex. For example, the presence of large biomolecule complex will lead to significant broadening of the particle size distribution curve. When used sequentially, either nanoparticle probe may be first mixed with sample solution to allow binding of the first biomolecule from the complex to the nanoparticle probe. Then a second probe is added to detect the second biomolecule in the complex. More nanoparticle probes may be added to the assay solution to detect additional binding partners in the complex.

As a special case of second embodiment, target molecule X and A are the same. In this case, biomolecular complex XA may also be called bimolecular aggregate (or may also be referred to as a homogenous complex). A larger aggregate can lead to larger particle size increase and/or broadened particle size distribution curve after the sample solution is in contact with at least one nanoparticle probe solution.

Reference to particle analysis may include, but is not limited to, determining a particle size change (including an individual particle size change), an average particle size change, particle size distribution change, polydispersity change of the size distribution, or measurement-to-measurement particle size variation, or combinations thereof. In a specific embodiment, particle analysis is conducted via DLS.

In a third embodiment, a nanoparticle without specific baiting molecule attached on the surface is mixed with a sample solution. Proteins and/or other biomolecules from the sample solution will be non-specifically adsorbed to the nanoparticle to form a biomolecule "corona". Gold or silver nanoparticles possess a charge that will allow them to non-specifically adsorb biomolecules. The size of this biomolecule corona, may be determined using dynamic light scattering or other suitable particle size analysis techniques. The size of this corona may be used to analyze a biological process, determine the disease status or reveal other physiological conditions of the sample donor. Furthermore, a second step assay may be conducted to reveal and quantify the individual biomolecules that are present in the biomolecule corona. If a target molecule X is present in the corona, the addition of an antibody or baiting molecule for molecule X to the assay solution will further increase the size of the particle, or cause particle cluster formation. Such particle size change can be correlated to the concentration or the size of molecule X in the sample solution. The concentration and/or size information of X can be used to analyze a biological process, determine the disease status or reveal other physiological conditions of the sample donor. Alternatively, if a target molecule D is not adsorbed to the nanoparticle, then the addition of a baiting molecule for D in the assay solution will not cause significant change of the nanoparticle size or formation of nanoparticle clusters.

EXAMPLES

In the following, three examples are given for each of the embodiments as described above. Additionally, a fourth example is provided to describe how the biomolecular complexes discovered from our research can be used for diagnostic applications.

1. Detection of a Heterocomplex EGFR/Stat3/Src From a Pancreatic Cancer Cell Line, Panc-1 Cells Using the first embodiment (FIG. 1), we recently successfully studied the assembly of signaling molecules into complexes that promote signal transduction. In particular, the new invention permitted the detection of hitherto unknown heterocomplex formed from three proteins: epidermal growth factor receptor (EGFR), Stat3, and Src in the nuclei of a pancreatic cancer cell line, Panc-1. EGFR is an important regulator of cellular responses, including growth and survival. The attention from biomolecular researchers on EGFR protein has been enormous in part because there remains a significant gap in the understanding of the key molecular partners that serve this pathway and how they contribute to the overall associated cellular responses. From the molecular and biological perspectives, EGFR is involved in a large number of sophisticated events that support cellular processes. EGFR is found in the plasma membrane, cytosol and nuclei of cells. A full understanding of all aspects of the EGFR protein, not only its expression level, but also its activity regulation, translocation, structural changes and the interactions with other proteins is essential for developing an effective model relevant to the functional role of this pathway in the overall biological phenotype. A study by J. Turkson et al. revealed that concurrent targeting of three proteins, EGFR, Stat3 and Src can enhance the therapeutic effect on pancreatic cancer. It was hypothesized based on their studies that EGFR, Stat3 and Src may have formed a heterocomplex nuclei and this complex functions as a transcript factor to regulate the cell growth of Panc-1. An assay based on the first embodiment confirmed the existence of such a complex in Panc-1 cell nuclei.

Figure 4:
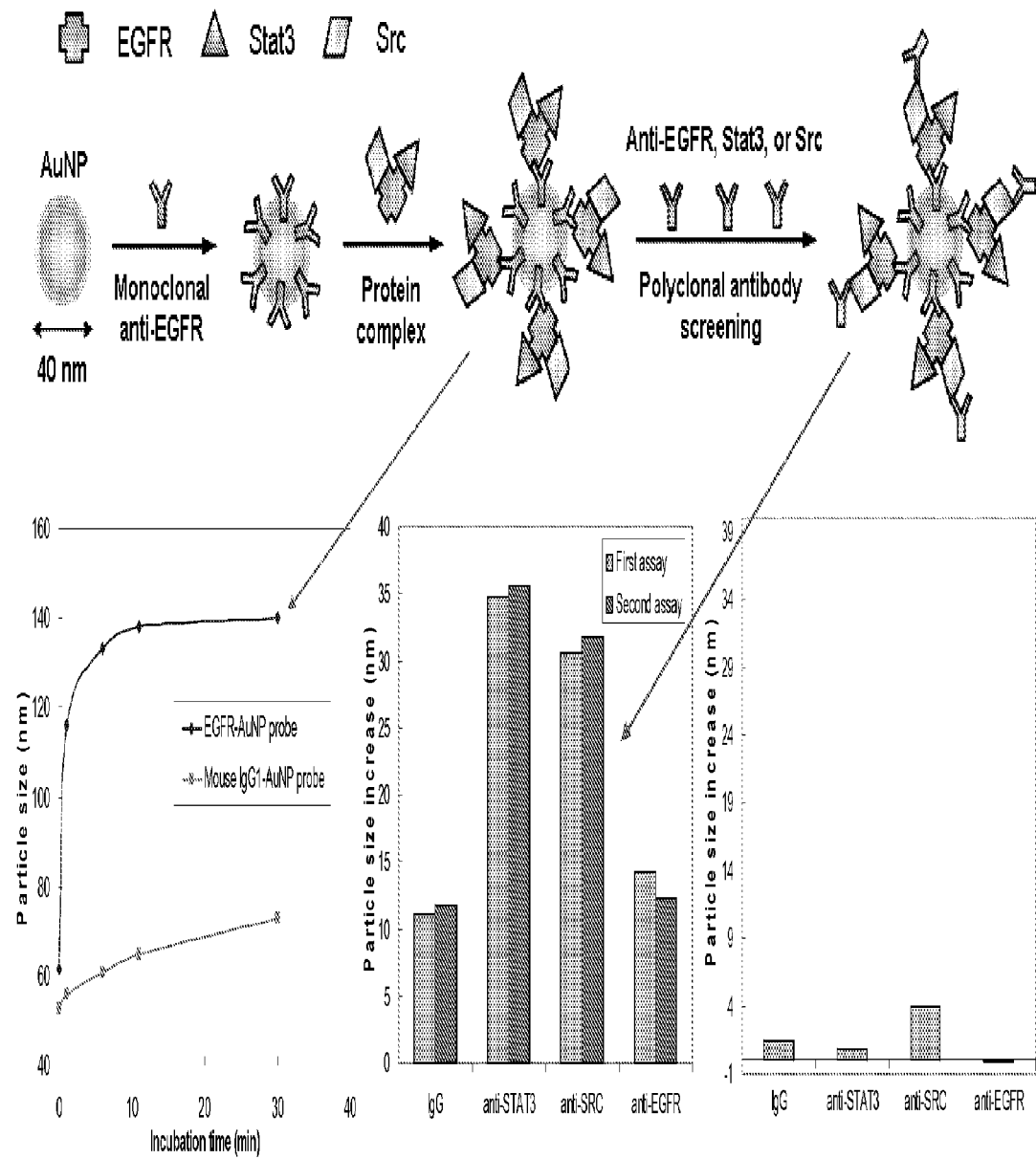
FIG. 4. (A) An illustration of an assay for protein complex detection and binding partner analysis from a cell nuclear extract. The assay was comprised of two steps: in the first step, AuNP immunoprobe for one target protein, here is EGFR, is mixed with a sample solution. The particle size increase caused by the binding of EGFR protein or protein complex to AuNP probes is monitored. After the binding event reaches an end point, the assay solution was divided into multiple portions and to each portion, a polyclonal antibody for each suspected protein binding partner was added to the assay solution. The particle size increase of the assay solution was then monitored and used to identify the binding partner. (B) Kinetic binding assay of EGFR-AuNP probe for mouse IgG1-AuNP probe was used as a negative isotype control to the EGFR-AuNP probe) with EGFR protein and its complex from a pancreatic cancer cell line, Panc-1 nuclear extracts. (C) and (D) Protein complex binding partner analysis whereby the polyclonal anti-Stat3, anti-Src or anti-EGFR antibody or the non-specific rabbit IgG (negative control) is added to the assay solution prepared from the anti-EGFR-AuNP probe (C) or non-specific mouse IgG1-AuNP probe (negative control) (D). Data are representative of 4 independent studies.

A mouse monoclonal antibody, anti-EGFR, was conjugated to AuNP to form EGFR-AuNP probe. Upon mixing this probe solution with Panc-1 nuclear lysate, the particle size increased rapidly from ca. 60 nm to 140 nm, while a non-specific isotype control mouse IgG1-conjugated to AuNP exhibits only about 10 nm of size increase after the assay (FIG. 4B). The rapid increase of the nanoparticle probe size corresponds to specific binding of target protein EGFR to the probe, while the slow and small size increase of mouse IgG1-AuNP probe is indicative of non-specific interactions.

The net increase of the anti-EGFR-AuNP probes after deducting the size increase caused by non-specific interactions, is about 70 nm. This suggests that the size of the EGFR protein complex detected by the anti-EGFR-AuNP probe is approximately 35 nm. EGFR protein has a molecular mass of 170 KDa. The size of EGFR protein alone should be between 10-45 nm. Therefore, data shown in FIG. 4B suggests that the EGFR detected by the nanoparticle probe is most likely in a complex form. In a second step assay, when a polyclonal anti-Stat3 or anti-Src was added to the assay solution, the nanoparticle size increased further by 30-35 nm; while the addition of isotype control rabbit IgG and anti-EGFR caused much less nanoparticle size increase (FIG. 4C). The substantial size increase from the addition of anti-Stat3 and anti-Src suggests that Stat3 and Src are binding partners in the EGER complex. The small size increase of the assay solution upon addition of anti-EGFR probe is due to the fact that Stat3 and Src in the complex blocked the binding sites of anti-EGFR to the nanoparticle-bound EGFR protein. The EGFR/Stat3/Src complex was further confirmed by co-immunoprecipitation followed by immunoblotting and laser scanning confocal microscopic analysis.

Co-immunoprecipitation is considered as the gold standard for protein complex detection from biological samples. However such analysis requires a substantial amount of samples (100s μL) and the analysis takes hours to days to complete. SPR technique also requires 10s-100s μL of sample per analysis. As a comparison, our new assay requires 1-2 μL of lysate samples and results are obtained in minutes. More importantly, neither co-immunoprecipitation, nor fluorescence technique, nor SPR is able to reveal the size information of the EGFR-Stat3-Src complex. Such information is particularly useful for protein complex analysis: it gives the first evidence of the presence of a protein complex, and can further reveal how many binding partners are involved in a protein complex. According to the assay results obtained so far, we believe the complex involves EGFR, Stat3 and Src only, because the estimated hydrodynamic diameter of such a triple-component complex according to each protein's size is around 35 nm, corresponds to the observed size from the assay.

2. Protein Aggregate Detection and Quantitative Analysis

Protein aggregate formation is a significant and challenging problem in biopharmaceutical development. To use proteins as therapeutic agents, they need to be formulated into high concentration solutions. Unfortunately, many proteins tend to aggregate at high concentrations. Once protein is aggregated, it can cause significant adverse effects by changing the pharmacokinetics of the drug or inducing unexpected immunogenicity. Protein aggregation is also closely associated to many diseases such as prion protein aggregates in Creutzfeldt-Jakob disease (CJD) and amyloid β-protein aggregates found in Alzheimer's disease. However, techniques that are available for direct detection and analysis of protein aggregation are extremely limited, especially for the detection of protein aggregates from complex biological samples and fluids in the presence of non-target proteins, biomolecules, and other colloidal particles. One widely used approach is by fluorescence techniques. Fluorescent probes are conjugated to the target protein by covalent bonding. Upon protein aggregation, fluorescent probe molecules will also aggregate, causing fluorescence signal change. A significant drawback of the fluorescence techniques is the need to do a fluorescence labeling of the target molecule. Other commonly used techniques for protein aggregate detection include size exclusion chromatography (SEC) and analytical ultracentrifugation. These techniques are only suitable for pure protein solution study, not suitable for detection of protein aggregates and complexes directly from real biological samples.

Figure 5:
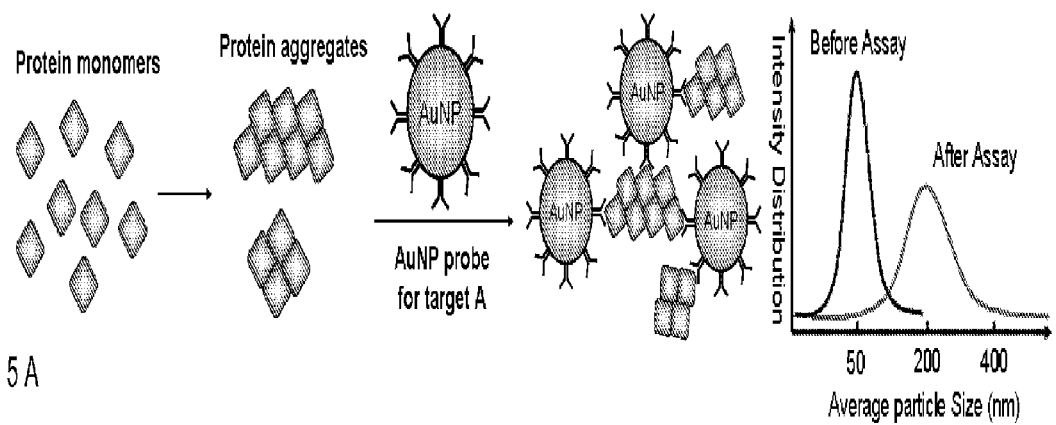
FIG. 5 (A) An illustration of gold nanoparticle immunoprobe cluster formation due to their binding with protein complexes or aggregates. (B) From the nonlinear dose-response curve, the concentration at which substantial GAPDH protein aggregation appears is identified. (C) and (D) The particle size distribution curves of the GAPDH assay solution at 25 and 50 μg/mL, respectively.
Figure 5:
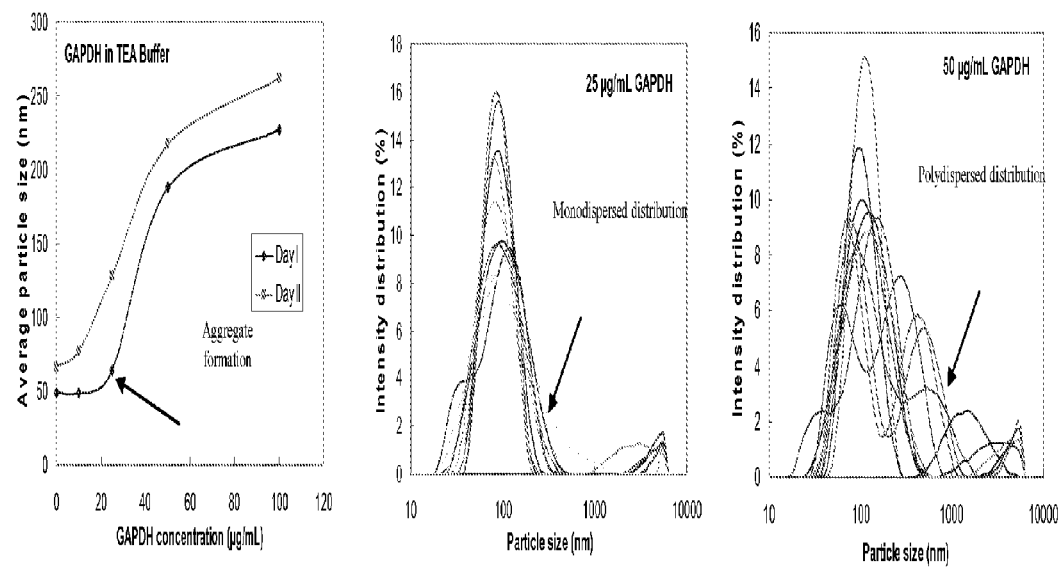

We have demonstrated that a new assay as illustrated in the second embodiment (FIG. 2) can be used as a label-free technique for highly sensitive detection of protein aggregates. In Rayleigh scattering, the scattered light intensity is proportional to the sixth power of the radius ($I \propto R^6$) of a particle. When protein complexes or aggregates with a non-uniform size distribution are present in a sample solution, these complexes/aggregates will load to the formation of large nanoparticle clusters as shown in FIG. 5A. The scattered light intensity from the large AuNP clusters is thousands to millions times stronger than individual AuNPs (the detection limit for individual AuNPs by DLS can already reach pM-aM range). Protein aggregation can be detected with extremely high sensitivity through the amplification of AuNP probes. Results shown in FIG. 5B-D are from our study on an enzyme GAPDH (glyceraldehyde 3-phosphate dehydrogenase, a protein used routinely as a loading control in Western Blot analysis). From the assay, we discovered that this protein has a strong tendency to form large aggregates at a concentration around 10-25 μg/mL. The protein aggregate formation leads to a non-linear and abnormal nanoparticle size increase around this concentration (FIG. 5B), and significant broadening or even peak splitting of the size distribution curves (Compare FIG. 5D with FIG. 5C).

Figure 6:
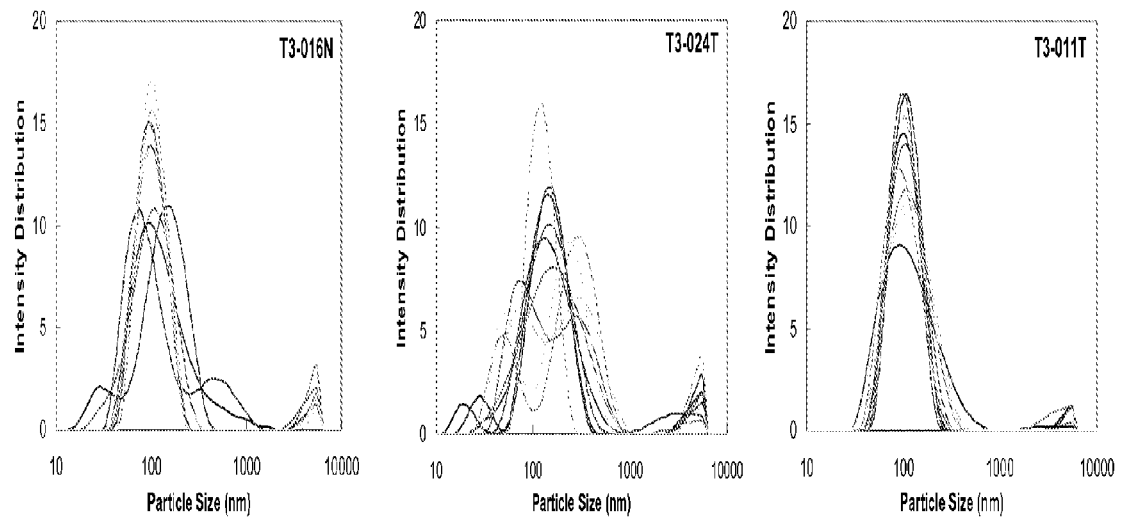
FIG. 6 (A) The size distribution curves of assay solutions from a normal prostate, prostate adenocarcinoma, and benign prostate hypertrophy (BPH) tissue lysate sample. Data presented in each graph are intensity distribution curves of an assay solution from ten measurements. (B) The polydispersity index (PdI) of the assay solutions from each sample. The numbers on top of the prostate cancer sample data are the Gleason sum score of the tissues. All data presented here are the average of ten measurements.
Figure 6:
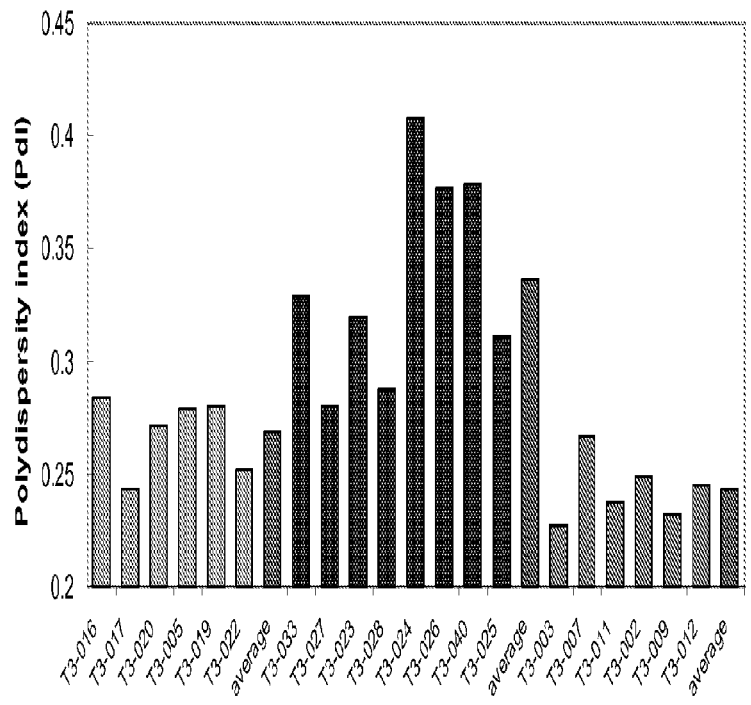

Furthermore, by using this new assay, we discovered that a cancer biomarker protein, prostatic acid phosphatase (PAP) exists more in the form of biomolecular complexes in cancer tissue than in normal and benign prostate hyperplasia (BPH) tissue. For this assay, an anti-PAP antibody is conjugated to AuNPs to make a nanoparticle immunoprobe. As shown in FIG. 6A, the particle size distribution curves from prostate cancer tissue lysate assay solution are substantially more broadened than BPH samples, and a significant amount of large nanoparticle clusters appeared at 100s nm size range. Such broad particle size distribution and the appearance of large nanoparticle clusters are explained by the presence of PAP protein in the form of large biomolecular complexes or aggregates. The level of particle size distribution curve broadening can be quantitatively expressed using a polydispersity index (PdI). As shown in FIG. 6B, the PdI of assay solutions obtained from prostate cancer tissue lysates is clearly higher than the assay solutions of normal prostate and BPH tissue lysates. Interestingly, BPH tissue lysate assay solutions exhibit a narrower particle size distribution than normal tissue lysates, indicating that a different molecular mechanism is involved in BPH than in prostate cancer. Furthermore, it appears that more advanced prostate cancer with higher Gleason scores leads to a higher complexing level of PAP protein. To our best knowledge, this is the first time that such molecular profile differences were revealed from biological samples and the potential link of such differences with cancer status of a biological system was discovered.

3. Serum Protein and Protein Complex Detection and Profiling for Diagnosis

Using the third embodiment as illustrated in FIG. 3, we discovered some very interesting and intriguing molecular differences between serum samples with and without prostate cancer from both mice models and human donors. Prostate cancer is one of the most prevalent types of cancer in men. It is estimated that 217,730 men will be diagnosed with and 32,050 men will die of prostate cancer in 2010. Despite the enormous research efforts and investigations, early detection and diagnosis of prostate cancer has remained a significant challenge in medicine due to multiple complicated factors. PSA test, a test that measures the level of prostate specific antigen in blood, has been widely used in the United States in the last two decades for initial screening of prostate cancer. However, several recent studies have led to significant doubts on the efficacy of PSA test. Over-diagnosis and treatment of low-risk prostate cancer has serious and long-lasting side effect: 33% of the patients who receive radical prostatectomy treatment will suffer erectile dysfunction that cannot be remedied by drugs such as Viagra. New biomarkers and test methods that can reliably distinguish prostate cancer from benign conditions and slow growing tumor from high risk cancer are of tremendous value in prostate cancer diagnosis and treatment.

Figure 7:
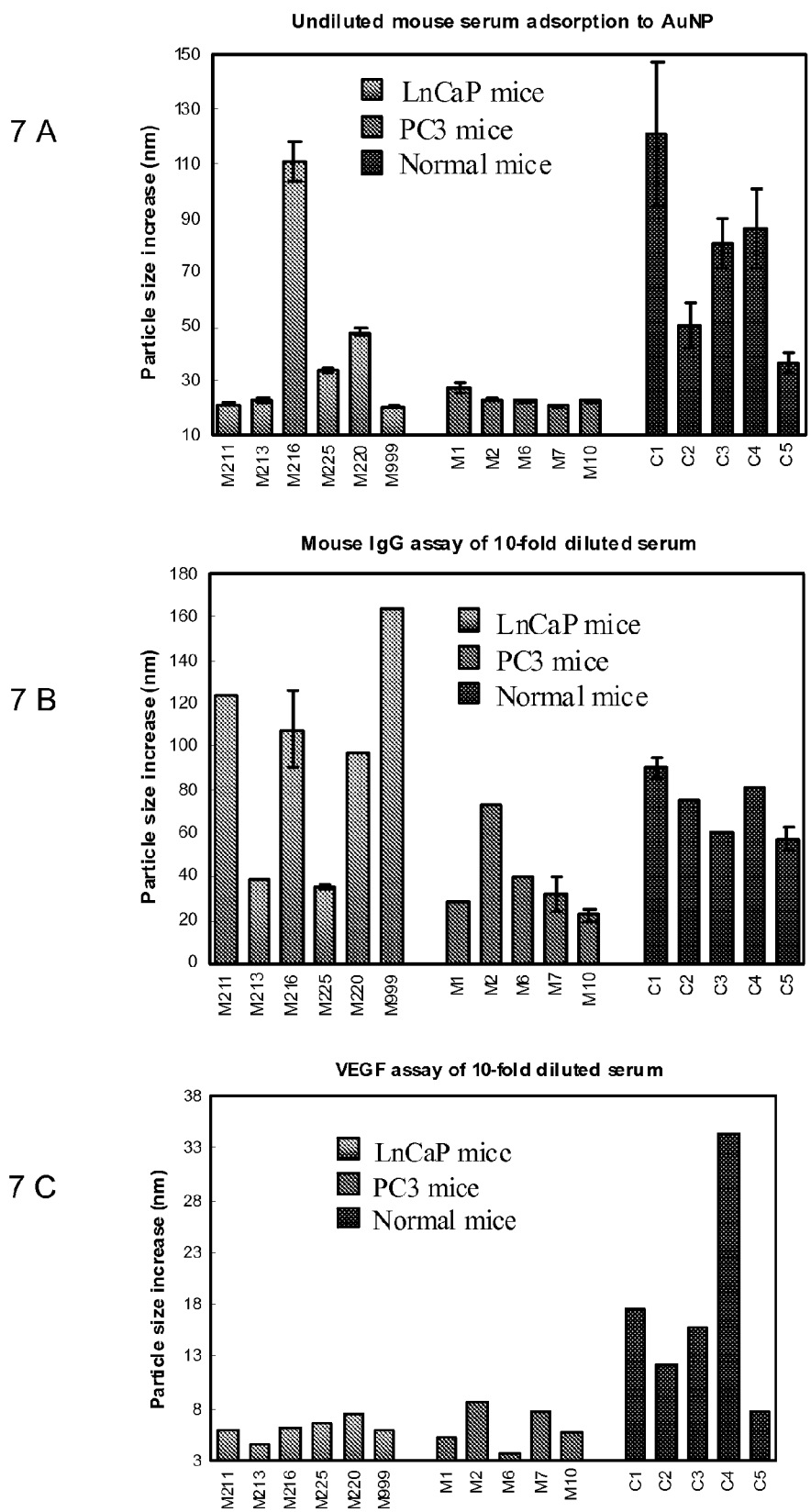
FIG. 7 Mouse serum protein adsorption study and target protein analysis. Data are particle size increases of the assay solution of: (A) undiluted mouse serum adsorbed to AuNPs; (B) IgG assay of 10-fold diluted mouse serum; (B) VEGF assay of 10-fold diluted mouse serum. For each assay, 40 μL of AuNP solution was mixed with 2 μL of serum sample. After certain incubation time, an appropriate amount of anti-mouse IgG or anti-VEGF was added to the assay solution to analyze the level of IgG or VEGF adsorbed to AuNPs.

Three mice models were used for this study: one was orthotopically injected with a fast growing prostate cancer cell line PC3; one with a slow growing tumor cell line LnCaP; and a third group of mice injected only with PBS saline solution as control. FIG. 7 are the analysis results of mice serum samples. First, there is a dramatic difference in the "size" of the proteins or protein complexes adsorbed from serum to AuNPs (FIG. 7A). The particle sizes from mice with large and fast growing tumor from PC3 cells are substantially smaller than that from normal healthy mice and mice with small and slow growing tumor from LnCaP cells. When the serum samples were diluted 10-fold and the serum protein adsorption assay was repeated, all samples exhibited similar particle size increase of 15-18 nm after the assay.

Figure 8:
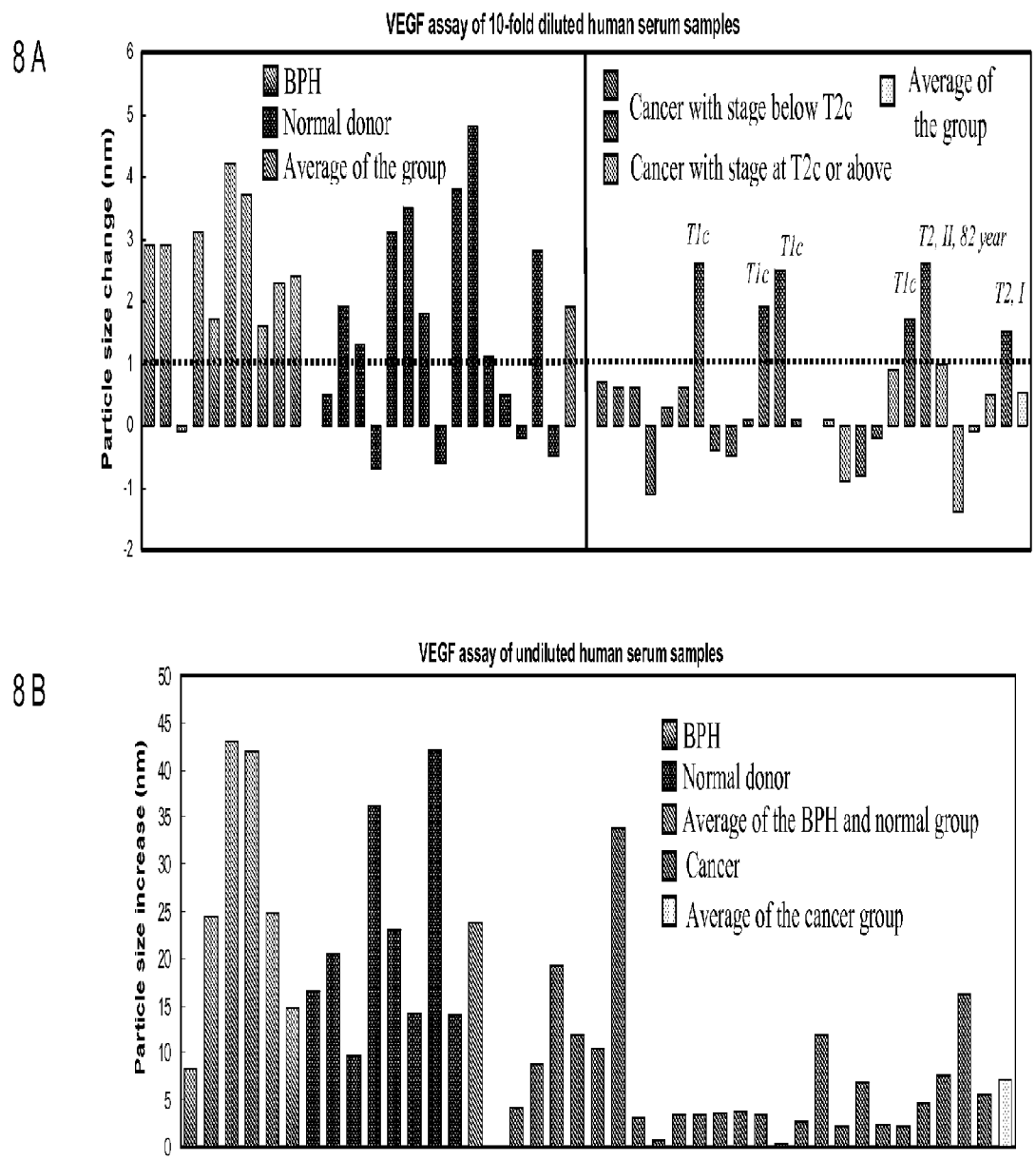
FIG. 8 VEGF assay results of 10-fold diluted (A) and undiluted (B) human serum samples from cancer and non-cancerous donors. The non-cancerous donors include normal and BPH patients. 40 μL of AuNP solution was mixed with 2 μL of serum sample. After certain incubation time, 2 μL anti-VEGF solution (0.5 mg/mL) was added. The particle size increase is the size difference measured before and after the addition of antibody. In A, the small legends on some samples such as T1c are the stage of the prostate cancer. Samples with a cancer stage of T2c or above are labeled with a cyan color. The average particle size change of all cancer samples minus the six early stage cancer samples is zero.

The inventor then analyzed two target proteins: one is an abundant protein, mouse IgG, and another one is a well known cancer biomarker protein, VEGF (vascular endothelial growth factor) according to the assay process as illustrated in FIG. 3. Again, some interesting differences were observed from these two assays. In the IgG assay, mice with small tumor grown from LnCaP cells exhibit higher level of IgG than the other two groups (FIG. 7B). In the VEGF assay, the normal healthy mice exhibit significantly higher level of AuNP-adsorbed VEGF than the mice with prostate cancer (FIG. 7C). Intrigued by the results observed from mice model study, we examined human serum samples obtained from subjects with prostate cancer. Three groups of human serum samples were studied: normal healthy donors; patients diagnosed with benign prostate hyperplasia (BPH); and patients diagnosed with prostate cancer (stages T1c to T3b). From the VEGF assay, same difference was observed from the cancer versus non-cancer samples (normal donor and BPH patients) (FIG. 8): the non-cancer samples show higher level of AuNP-adsorbed VEGF level than the prostate cancer samples. T-test analysis of the assay data gave a p-value of 0.001 for both diluted and undiluted human serum samples, indicating that the difference between cancer and non-cancerous samples was statistically significant. Furthermore, it was found from the assay that the AuNP-adsorbed VEGF level is also cancer stage-dependent: the more advanced prostate cancer exhibits lower VEGF level than the early stage prostate cancer. Early stage prostate cancer such as T1c shows similar VEGF level as healthy donors. In conclusion, the analysis of both mice model and human donor samples revealed that the amount of AuNP-adsorbed VEGF is decreased in cancer serum samples. This discovery could potentially lead to a new blood test with improved accuracy for prostate cancer detection. Furthermore, by screening other proteins or bimolecular targets using this assay, it is expected that additional protein or biomolecular biomarkers that are unique to cancer and other human diseases can be discovered. This new assay established in our recent work may be used as a general tool for serum protein biomarker discovery.

4. The Use of Biomolecular Complexes as Biomarkers for Diagnostic Applications

There are several types of biomarkers that have been identified so far and can be used for prostate cancer detection and diagnosis, particularly, for distinguishing prostate cancer from non-malignant conditions such as BPH: (1) The increased complexing level of PAP protein in tissue and bodily fluids; (2) The decreased level of VEGF protein in blood samples. This VEGF protein is referred to VEGF protein that is adsorbed to a nanoparticle through complexing with other proteins or biomolecules present in the blood serum; (3) The size of the biomolecule corona formed on a nanoparticle surface after non-specific adsorption of biomolecules from a biological sample to the nanoparticles.

The claims for biomarkers may be extended to the detection and diagnosis of other diseases and conditions: (1) The size of the biomolecule corona formed on a nanoparticle surface after a non-specific adsorption of biomolecules from a biological sample to the nanoparticles; (2) The size of the biomolecule corona formed on a nanoparticle surface after a specific binding of biomolecules from a biological sample to the baiting molecule-conjugated nanoparticles; (3) Individual molecule component or biomolecule complexes of the biomolecule corona formed on a nanoparticle surface after a non-specific adsorption or specific binding of biomolecules from a biological sample to the nanoparticles that show significant difference between diseased and non-diseased samples.

REFERENCES

1. Liu, X.; Dai. Q.; Austin, L.; Coutts, J.; Knowles, G.; Zou, J.; Chen, H.; Huo, Q. A One-step homogeneous immunoassay for cancer biomarker detection using gold nanoparticle probes coupled with dynamic light scattering. J. Am. Chem. Soc. 2008, 130, 2780-2782.
2. Dai, Q.; Liu, X.; Coutts, J.; Austin, L.; Huo, Q. A one-step highly sensitive method for DNA detection using dynamic light scattering. J. Am. Chem. Soc. 2008, 130, 8138-8139.
3. Liu, X.; Huo, Q. A washing-free and amplification-free one-step homogeneous assay for protein detection using gold nanoparticle probes and dynamic light scattering. J. Immunol. Method 2009, 349, 38-44
4. Jans, H.; Liu, X.; Austin, L.; Maes, G.; Huo, Q. Dynamic light scattering as a powerful tool for gold nanoparticle bioconjugation and biomolecular binding study. Anal. Chem. 2009, 81, 9425-9432.
5. Austin, L.; Liu, X.; Huo, Q. An immunoassay for monoclonal antibody isotyping and quality analysis using gold nanoparticles and dynamic light scattering. 2010, American Biotechnology Laboratory, 2010, 22, No. 3, 8-12.
6. Bogdanovic, J.; Huo, Q. NanoDLSay: a new platform technology for biomolecular detection and analysis using gold nanoparticle probes coupled with dynamic light scattering. SPIE Proceedings, (2010), 7674 (Smart Biomedical and Physiological Sensor Technology), 767408/1-767408/9.
7. Bogdanovic, J.; Colon, J; Baker, C.; Huo, Q. A label-free nanoparticle aggregation assay for protein complex/aggregate detection and analysis. Anal. Biochem. 2010, 405, 96-102.
8. Huo, Q. Protein complexes/aggregates as potential cancer biomarker revealed by a nanoparticle aggregation immunoassay. Colloids Surf B. 2010, 78, 259-265.
9. Jaganathan, S.; Yue, P.; Bogdanovic, J.; Huo, Q.; Turkson, J. A functional nuclear epidermal growth factor receptor, Src and Stat3 heteromeric complex in pancreatic cancer cells. *Plos* One, 2010, submitted.
10. Huo, Q.; Cordero, A.; Bogdanovic, J.; Colon, J.; Baker, C. H.; Goodison, S.; Pensky, M. A facile nanoparticle immunoassay to detect multiple biomarkers in serum samples. Nanomedicine: Nanotechnology, Biology and Medicine, 2010, submitted.

It should be borne in mind that all patents, patent applications, patent publications, technical publications, scientific publications, and other references referenced herein are hereby incorporated by reference in their entirety to the extent not inconsistent with the teachings herein.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:
1. A method for detecting a biomolecule complex in a biological sample, said method comprising
producing a first assay product by contacting a biological sample with a first nanoparticle probe, said first nano- particle probe comprising a nanoparticle bound to a first baiting molecule specific to a first target molecule of interest;

contacting the first assay product with a second baiting molecule specific to a second target molecule of interest to produce a second assay product; and detecting by particle analysis for presence of nanoparticle probe bound to said first target molecule of interest, or for presence of said second target molecule of interest in said second assay product, or both, wherein if both, a complex of the first and second target molecules is present in the biological sample.

2. The method of claim 1, wherein particle analysis comprises determining a particle size change, an average particle size change, particle size distribution change, polydispersity change of the size distribution, or measurement-to-measurement particle size variation, or combinations thereof.

3. The method of claim 1, wherein said particle analysis is by dynamic light scattering analysis.

4. The method of claim 1, wherein the particle analysis comprising determining a particle size change over nanoparticle probe-sample incubation time or over first target molecule concentration is used to obtain the binding constant or binding energy between the first baiting molecule and the first target molecule.

5. The method of claim 4, wherein the binding constant or binding energy is obtained by fitting the binding data into a Langmuir adsorption model.

6. The method of claim 1, further comprising determining whether a first target molecule is a monomer based on particle analysis.

7. The method of claim 6, further comprising determining the quantity of a biomolecule complex based on particle analysis; or determining the size of a biomolecule complex based on particle analysis.

8. The method of claim 7, further comprising utilizing a quantity of a biomolecule complex to analyze a biological process, or for detection, diagnosis and/or prognosis of a disease; or utilizing the size of a biomolecule complex to analyze a biological process, or for detection, diagnosis and/or prognosis of a disease.

9. The method of claim 8, wherein the disease is cancer.

10. The method of claim 6, wherein the biomolecule complex is a complex of PAP (prostatic acid phosphatase).

11. The method of claim 1, wherein said biomolecule complex comprises at least one first biomolecule or first biomolecule subunit associated with at least one other biomolecule.

12. The method of claim 11, wherein said at least one other biomolecule is the same as the first biomolecule or first biomolecule subunit.

13. The method of claim 1, wherein said detecting comprises subjecting said second assay product to particle analysis.

14. A method for detecting a target molecule in a biological sample, said method comprising
(a) obtaining a first assay product that has been produced by contacting a biological sample with a first nanoparticle probe, said first nanoparticle probe comprising a nanoparticle bound to a first baiting molecule specific to a first target molecule of interest;
(b) subjecting said first assay product to a second nanoparticle probe comprising a second baiting molecule that is specific to a second target molecule of interest to produce a second assay product; and
(c) detecting for presence of second nanoparticle probe bound to said second target molecule of interest in said second assay product, wherein if the second nanoparticle probe bound to said second target molecule of interest is detected, the second target molecule of interest is present in the biological sample; and further comprising detecting presence of first nanoparticle probe bound to said first target molecule of interest in said first assay product before step (c), wherein a biomolecule complex of said first and second target molecules of interest is detected based on a difference in size between said first assay product and said second assay product.

15. A method for detecting at least one biomolecule in a biological sample, said method comprising obtaining a first assay product produced by contacting a biological sample with a nanoparticle, wherein said contacting forms a biomolecule corona on the nanoparticle surface, and conducting particle analysis of the first assay product; and further comprising (i) using biomolecule corona size information for detection, diagnosis and/or prognosis of a disease by comparing the biomolecule corona size information with size information from a known sample, or (ii) contacting said first assay product with a baiting molecule that binds specifically to a target molecule of interest to form a second assay product, and detecting the presence and/or quantity of the target molecule of interest by particle analysis.

16. The method of claim 15, wherein said analysis comprises size analysis of the biomolecule corona.

* * * * *